(12) United States Patent
Feld

(10) Patent No.: US 10,583,237 B2
(45) Date of Patent: Mar. 10, 2020

(54) CONTINUOUS IMPLANTABLE PERITONEAL DIALYSIS

(71) Applicant: Paragate Medical Ltd., Nazareth (IL)

(72) Inventor: Yair Feld, Haifa (IL)

(73) Assignee: Paragate Medical Ltd., Nazareth (IL)

( * ) Notice: Subject to any disclaimer, the term of this patent is extended or adjusted under 35 U.S.C. 154(b) by 229 days.

(21) Appl. No.: 15/319,000

(22) PCT Filed: Jun. 14, 2015

(86) PCT No.: PCT/IL2015/050598
§ 371 (c)(1),
(2) Date: Dec. 15, 2016

(87) PCT Pub. No.: WO2015/193880
PCT Pub. Date: Dec. 23, 2015

(65) Prior Publication Data
US 2017/0128654 A1    May 11, 2017

Related U.S. Application Data

(60) Provisional application No. 62/012,381, filed on Jun. 15, 2014.

(51) Int. Cl.
*A61M 1/28* (2006.01)
*A61M 25/00* (2006.01)
(Continued)

(52) U.S. Cl.
CPC .............. *A61M 1/285* (2013.01); *A61M 1/28* (2013.01); *A61M 25/0041* (2013.01);
(Continued)

(58) Field of Classification Search
CPC .... A61M 1/28; A61M 1/285; A61M 25/0041; A61M 25/10; A61M 27/008
See application file for complete search history.

(56) References Cited

U.S. PATENT DOCUMENTS

| | | |
|---|---|---|
| 3,707,967 A | 1/1973 | Kitrilakis et al. |
| 4,437,856 A | 3/1984 | Valli |
| (Continued) | | |

FOREIGN PATENT DOCUMENTS

| | | |
|---|---|---|
| CN | 1469760 | 1/2004 |
| CN | 101389373 | 3/2009 |
| (Continued) | | |

OTHER PUBLICATIONS

Notification of Office Action and Search Report dated Jun. 4, 2018 From the State Intellectual Property Office of the People's Republic of China Re. Application No. 201580031804.0. (7 Pages).
(Continued)

*Primary Examiner* — Ariana Zimbouski

(57) ABSTRACT

A system and method for draining excessive fluid from a body cavity or space. The system comprises an implantable fluid penetrable chamber comprising a frame covered by a fluid permeable mesh configured to enable fluids to penetrate therethrough. The system further comprises a catheter connected at a first end to one of said chamber sides/walls or penetrates therethrough; and optionally further comprises a pump placed inside or outside of said chamber.

19 Claims, 4 Drawing Sheets

(51) Int. Cl.
*A61M 25/10* (2013.01)
*A61M 27/00* (2006.01)

(52) U.S. Cl.
CPC .......... *A61M 25/10* (2013.01); *A61M 27/008* (2013.01); *A61M 2205/04* (2013.01); *A61M 2205/75* (2013.01); *A61M 2210/1021* (2013.01); *A61M 2210/1085* (2013.01)

(56) References Cited

U.S. PATENT DOCUMENTS

| | | | |
|---|---|---|---|
| 4,490,137 | A | 12/1984 | Moukheibir |
| 5,254,084 | A | 10/1993 | Geary |
| 5,902,336 | A | 5/1999 | Mishkin |
| 6,296,668 | B1 | 10/2001 | Desgrandchamps et al. |
| 6,569,130 | B1 | 5/2003 | Levin |
| 7,309,323 | B2 | 12/2007 | Gura et al. |
| 8,012,118 | B2 | 9/2011 | Curtin et al. |
| 8,632,489 | B1 | 1/2014 | Ahmed |
| 8,641,659 | B2 | 2/2014 | Soykan et al. |
| 9,060,888 | B2 * | 6/2015 | Gellman ............... A61F 2/88 |
| 2003/0109855 | A1 | 6/2003 | Solem et al. |
| 2004/0167634 | A1 * | 8/2004 | Atala ............. A61L 27/3804 623/23.65 |
| 2005/0096582 | A1 | 5/2005 | Burnett |
| 2007/0197957 | A1 * | 8/2007 | Hunter ............... A61L 31/10 604/65 |
| 2008/0051696 | A1 | 2/2008 | Curtin et al. |
| 2009/0318844 | A1 * | 12/2009 | Burnett ............. A61M 27/002 604/9 |
| 2010/0121159 | A1 * | 5/2010 | Burnett ............... A61B 5/01 600/301 |
| 2011/0071415 | A1 | 3/2011 | Karwosky et al. |
| 2011/0208319 | A1 | 8/2011 | Laster |
| 2012/0220926 | A1 * | 8/2012 | Soykan .............. A61M 1/284 604/28 |
| 2013/0211322 | A1 | 8/2013 | Degen et al. |
| 2013/0253409 | A1 | 9/2013 | Burnett |
| 2014/0066841 | A1 | 3/2014 | Degen et al. |
| 2014/0148754 | A1 | 5/2014 | Soykan et al. |
| 2017/0007808 | A1 | 1/2017 | Dalton |

FOREIGN PATENT DOCUMENTS

| | | |
|---|---|---|
| WO | WO 98/16171 | 4/1998 |
| WO | WO 98/50088 | 11/1998 |
| WO | WO 02/32479 | 4/2002 |
| WO | WO 2006/023589 | 3/2006 |
| WO | WO 2008/055248 | 5/2008 |
| WO | WO 2009/025807 | 2/2009 |
| WO | WO 2011/113615 | 9/2011 |
| WO | WO 2011/141815 | 11/2011 |
| WO | WO 2012/112932 | 8/2012 |
| WO | WO 2015/193880 | 12/2015 |
| WO | WO 2017/015351 | 1/2017 |
| WO | WO 2018/211500 | 11/2018 |

OTHER PUBLICATIONS

Flessner "Net Ultrafiltration in Peritoneal Dialysis: Role of Direct Fluid Absorption Into Peritoneal Tissue", Blood Purification, 10(3-4): 136-147, 1992.
International Preliminary Report on Patentability dated Dec. 22, 2016 From the International Bureau of WIPO Re. Application No. PCT/IL2015/050598. (7 Pages).
International Search Report and the Written Opinion dated Oct. 28, 2015 From the International Searching Authority Re. Application No. PCT/IL2015/050598.
Supplementary European Search Report and the European Search Opinion dated Jan. 5, 2018 From the European Patent Office Re. Application No. 15809620.6. (8 Pages).
Translation Dated Jun. 14, 2018 of Notification of Office Action dated Jun. 4, 2018 From the State Intellectual Property Office of the People's Republic of China Re. Application No. 201580031804.0. (4 Pages).
Notification of Office Action and Search Report dated Jan. 14, 2019 From the State Intellectual Property Office of the People's Republic of China Re. Application No. 201580031804.0 and Its Summary in English. (6 Pages).
Translation Dated Jan. 22, 2019 of Notification of Office Action dated Jan. 14, 2019 From the State Intellectual Property Office of the People's Republic of China Re. Application No. 201580031804.0. (1 Page).
International Search Report and the Written Opinion dated Oct. 22, 2018 From the International Searching Authority Re. Application No. PCT/IL2018/050525. (23 Pages).
Invitation to Pay Additional Fees, Communication Relating to the Results of the Partial International Search and the Provisional Opinion dated Aug. 31, 2018 From the International Searching Authority Re. Application No. PCT/IL2018/050525. (20 Pages).
Erickson "Size and Shape of Protein Molecules at the Nanometer Level Determined by Sedimentation, Gel Filtration, and Electron Microscopy", Biological Procedures Online, XP055499868, 11(1): 32-51, May 15, 2009.
Communication Pursuant to Article 94(3) EPC dated Jul. 16, 2019 From the European Patent Office Re. Application No. 15809620.6. (5 Pages).
International Preliminary Report on Patentability dated Nov. 2019 From the International Bureau of WIPO Re. Application No. PCT/IL2018/050525. (14 Pages).

* cited by examiner

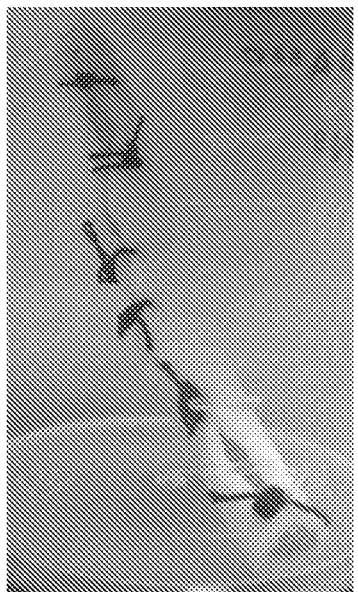 
Figure 4A
Figure 4B

CONTINUOUS IMPLANTABLE PERITONEAL DIALYSIS

RELATED APPLICATIONS

This application is a National Phase of PCT Patent Application No. PCT/IL2015/050598 having International filing date of Jun. 14, 2015, which claims the benefit of priority under 35 USC § 119(e) of U.S. Provisional Patent Application No. 62/012,381 filed on Jun. 15, 2014. The contents of the above applications are all incorporated by reference as if fully set forth herein in their entirety.

FIELD OF THE INVENTION

The present invention relates to the field of medical instruments. More particularly, the present invention relates to a device and method for assisting disposal of redundant bodily fluids and decreasing the need for dialysis. The present invention is particularly useful for improving the treatment of heart failure.

BACKGROUND OF THE INVENTION

Chronic kidney disease (CKD) and end stage renal disease (ESRD) are highly problematic for many people, as there is a shortage of convenient and/or readily available treatments. For example, dialysis may be performed on patients with failing kidneys to remove substances such as wastes, etc. from the patients' blood, however, often patients must connect to dialysis systems frequently. The need for such frequent dialysis treatments causes inconvenience and significantly reduces the patients' quality of life.

In contrast, for those who have undergone a kidney transplant operation, after the recovery period is complete, the quality of life increases in comparison to those needing dialysis treatment. However, kidney transplant operations are not a ready option for so many in need, due to the fact that the demand for healthy kidneys far exceeds the supply.

There is a substantial need for treating failing kidneys in a fashion that would negatively impact the patient's quality of life much less than frequent dialysis but would also be available to many persons in need at lower costs than that of kidney transplants. Even if for some patients a new treatment would not completely eliminate the need for dialysis, it could significantly reduce the frequency of the dialysis treatments.

U.S. Pat. No. 8,012,118 relates to a wearable dialysis system and method for removing uremic waste metabolites and fluid from a patient suffering from renal disease.

U.S. Pat. No. 5,902,336 relates to an implantable ultrafiltration device for removing low to medium molecular weight solutes and fluids from the blood of a patient experiencing renal failure. The device includes a pump having an inlet and an outlet; a first component for forming a first fluid flow path between the patient's vascular system and the pump inlet; a filter interposed in the first fluid flow path, the filter being permeable to water and substantially impermeable to blood cells and proteins; and a second component for forming a second fluid flow path between the pump outlet and the patient's bladder, wherein the pump, the first and second components, and the filter are all constructed to be surgically implanted in the patient's body.

US 2013/0253409 relates to a device for removing fluid from a first bodily cavity and for directing that fluid into a second bodily cavity while avoiding risks of infection and, in one embodiment, excessive dehydration of the first bodily cavity. The device includes a pump and a reservoir.

Prior art methods do not provide sufficient treatments for disposal of redundant fluids. It is therefore an object of the present invention to provide a method and means for assisting in the disposal of redundant bodily fluids.

It is a further object of the present invention to provide a method and means for decreasing the use of dialysis treatments.

Another object of the present invention to treat patients with heart failure that are also in need of fluids removal.

Other objects and advantages of the present invention will become apparent as the description proceeds.

SUMMARY OF THE INVENTION

The present invention relates to a system and method for disposing of redundant body fluids from the body. The present invention system comprises an implantable fluid-penetrable chamber that allows accumulating body fluids near the implant site to penetrate the chamber. The chamber is coupled to (and in fluid communication with) a tube element (e.g. catheter) that leads to a cavity of a urinary system organ or directly out of the bogy, e.g. through a stoma. The system enables delivering fluid from said chamber to said cavity of a urinary system organ (which leads to disposal) or to said stoma.

According to one embodiment, the urinary system organ is the renal pelvis. The pressure in the renal pelvis is influenced by the ureter. Since the renal pelvis is in fluid communication with the chamber, changes of the pressure in the renal pelvis lead to corresponding changes in pressure within the chamber. When the pressure in the pelvis becomes lower it leads to suction of fluid from the chamber to the pelvis. According to another embodiment, the urinary system organ is the bladder.

According to an embodiment of the present invention, a pump is also coupled to and in fluid communication with the chamber, and is capable of assisting fluid flow from the chamber to said cavity of a urinary system organ or to said stoma.

Tubular elements such as catheters, can interconnect and couple two or more elements of the system (e.g. chamber, pump) such that said two or more elements are all in fluid communication with each other. Optionally, the pump can attach directly to the chamber.

According to an embodiment of the present invention, the chamber comprises a frame covered by a fluid penetrable mesh. The frame may have various shapes and may comprise (strait or curved) rods or bars or (one or more) wires (or a combination thereof interconnected).

According to one embodiment the frame is a spiral coil with spring-like properties.

The present invention relates to a system comprising
an implantable fluid penetrable chamber comprising a frame covered by a fluid permeable mesh configured to enable fluids to penetrate therethrough;
a catheter connected at a first end to one of said chamber sides/walls or penetrates therethrough;
and optionally further comprising a pump placed inside or outside of said chamber.

Preferably, the volume of the chamber is capable of expanding and contracting in response to changes in pressure within the catheter and/or as result of the activity of the optional pump.

Preferably, the pump is connected between the chamber and the catheter.

Preferably, the pump is a peristaltic pump.

Preferably, the frame is a coil with spring-like properties such that said coil is configured to elastically contract and expand.

Preferably, the coil comprises biocompatible material.

Preferably, the coil is curved in the form of a spiral.

Preferably, the mesh is made of material selected from the group consisting of Teflon, Polypropylene, Polyester, ePTFE, titanium, omega 3, monocryl, PVDF, hyaluronate and Gortex, acellular collagen, pig collagen, a matrix derived from human dermis and porcine small intestine submucosa.

Preferably, the catheter is a pigtail catheter.

Preferably, the catheter is a straight catheter comprising an inflatable balloon attached at or near a second end of said catheter.

The present invention relates to a method for draining excessive fluid from a body cavity or space, said method comprising the steps of:

a) implanting a device within said body cavity or space; wherein said device comprises an implantable fluid-penetrable chamber comprising a frame covered by a fluid permeable mesh configured to enable fluids to penetrate therethrough;

a catheter connected at a first end to one of said chamber sides/walls or penetrates therethrough;

and optionally further comprising a pump placed inside or outside of said chamber;

b) positioning the second end of said catheter within the cavity of a urinary system organ;

such that changes in pressure within said catheter and/or changes in pressure exerted within said chamber by said optional pump result in the ingress of fluid from the body cavity or space into said chamber and/or the passage of said fluid from said chamber through said catheter into said urinary system organ cavity.

Preferably, the cavity of a urinary system organ is the renal pelvis.

Preferably, the cavity of a urinary system organ is the urinary bladder.

Preferably, the body cavity or space the abdominal cavity.

Preferably, the changes in pressure within the catheter and/or changes in pressure exerted within the chamber by the optional pump result in cyclical changes in the internal volume of the fluid-penetrable chamber, thereby correspondingly assisting the ingress of fluid from the body cavity or space into said chamber, and/or thereby correspondingly assist in the passage of the fluid from said chamber through said catheter into the urinary system organ cavity.

The present invention relates to a method for draining excessive fluid from a body cavity or space, said method comprising the steps of:

a) implanting a device within said body cavity or space; wherein said device comprises an implantable fluid penetrable chamber comprising a frame covered by a fluid permeable mesh configured to enable fluids to penetrate therethrough;

a catheter connected at a first end to one of said chamber sides/walls or penetrates therethrough;

and optionally further comprising a pump placed inside or outside of said chamber;

b) positioning the second end of said catheter within a stoma in the body wall;

such that changes in pressure within said catheter and/or changes in pressure exerted within said chamber by said optional pump result in the ingress of fluid from the body cavity or space into said chamber and/or the passage of said fluid from said chamber through the said body wall stoma connected to the second end of the catheter.

Preferably, the body cavity or space the abdominal cavity.

Preferably, the changes in pressure within the catheter and/or changes in pressure exerted within the chamber by the optional pump result in cyclic, changes in the internal volume of the fluid-penetrable chamber, thereby correspondingly assisting the ingress of fluid from the body cavity or space into said chamber, and/or thereby correspondingly assist in the passage of the fluid from said chamber through said catheter into the urinary system organ cavity.

The present invention relates to a system comprising
an implantable fluid penetrable chamber comprising a frame covered by a fluid permeable mesh configured to enable fluids to penetrate therethrough;
a tube element (e.g. catheter) connected at a first end to one said chamber sides/walls or penetrates therethrough.

The present invention relates to a system comprising
an implantable fluid penetrable chamber comprising a frame covered by a fluid permeable mesh configured to enable fluids to penetrate therethrough;
a tube element (e.g. catheter) connected at a first end to one of said chamber sides/walls or penetrates therethrough;
and further comprising a pump placed inside or outside of said chamber.

BRIEF DESCRIPTION OF THE DRAWINGS

The present invention is illustrated by way of example in the accompanying drawings, in which similar references consistently indicate similar elements and in which:

FIGS. 4A-4B illustrate images related to the device used in an experiment.

DETAILED DESCRIPTION OF THE INVENTION

Figure 1:
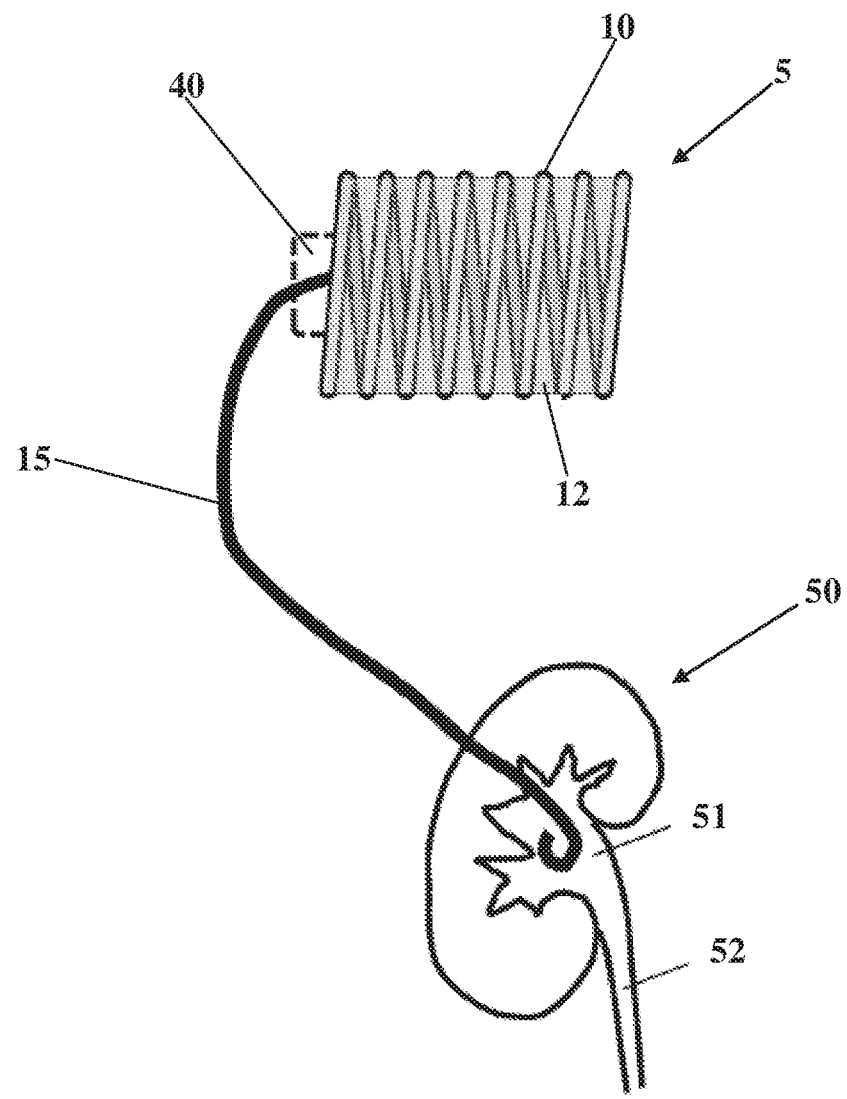
FIG. 1 illustrates an embodiment the present invention wherein one end of the catheter is inserted into the renal pelvis.

In certain medical conditions (including kidney failure) there is excessive fluid accumulation within the body, particularly within the abdominal cavity. The present invention provides means for removal of these fluids from that location and from the body. The removal of these redundant fluids decreases the reliance on kidney activity and decreases the need for dialysis treatment.

Embodiments of the present invention described herein function as artificial kidneys, which drain waste fluids, electrolytes, urea, and proteins from a patient's internal body cavity, such as the abdominal cavity, and thereby reduce or eliminate altogether the patient's reliance on his/her native kidney and/or dialysis. As explained in more detail below, the invention may be embodied as a device for draining substances from the body.

The present invention relates to a system comprising an implantable fluid-penetrable chamber that allows accumulating body fluids near the implant site to penetrate the chamber by pressure gradient (e.g. produced by an implanted pump or by the ureter peristaltic movement). Preferably, the implantable fluid-penetrable chamber is implanted in the abdominal cavity. A tube or catheter is connected at one end to one of the chamber sides/walls or penetrates through it to a location within the interior of the chamber. The tube or catheter enables transfer of the fluids accumulated in the chamber to different locations in the body that lead to disposal (e.g. urine system). Optionally, the tube or catheter leads out of the body (e.g. via a stoma), for direct disposal of the accumulated body fluids. The present invention is preferably implanted through Laparoscopy, but can also be implanted through other methods known in the art.

The chamber comprises a frame covered by a mesh that enables fluids to penetrate therethrough. The frame preferably comprises biocompatible material. According to one embodiment, the frame is comprised of flat permeable sides covered by meshes. According to another embodiment the frame is comprised of interconnected thin straight or curved rods/bars/wires which are covered by meshes forming 3 dimensional shape chambers. Preferably the chamber shapes have large surface areas (e.g. elliptic shape) allowing efficient fluid penetration. The mesh large surface area enables fluid suction into the chamber from the cavity it is placed within, and from the cavity surrounding tissue that it comes into contact with. The mesh material enables suction of the fluids directly from the tissue without requiring the tissue to first eject the fluid into the cavity. This is a major advantage in cases where treatment is required to dispose of redundant bodily fluids from tissues surrounding body cavities as well as from within the cavities themselves.

The mesh is a fluid permeable mesh such as a synthetic biocompatible mesh. The mesh is preferably made of material selected from the group consisting of Teflon, Polypropylene, Polyester, ePTFE, titanium, omega 3, monocryl, PVDF, hyaluronate and Gortex. The mesh can also be made of biological material such as acellular collagen, pig collagen, a matrix derived from human dermis, porcine small intestine submucosa, etc. Not only do these materials prevent tissue growth on the chamber, they assist in preventing tissue growth on the mesh.

Preferably, the frame comprises a curved bar/wire in the form of a coil.

According to one embodiment, the catheter or tube couples the interior of the chamber to the kidney pelvis. Continuous contractions of the ureter lower the fluid pressure within the kidney pelvis, and because the kidney pelvis interior is in fluid communication with the chamber interior by virtue of the catheter or tube, the continuous ureter contractions cause a reduction of pressure in the interior of the chamber. Thus the fluid content in the interior of the chamber flows through the catheter/tube into the interior of the kidney and thence through the ureter, bladder, urethra and is thus ultimately eliminated from the body.

After the ureter stops contracting, the pressure inside the kidney pelvis is relatively low and begins accumulating, fluids start to accumulate therein and the pelvis returns to its (higher) baseline pressure level. The pressure within the interior of the chamber (in fluid communication with pelvis) correspondingly increases.

Especially during the times within the ureter cycle following the ureter acting to reduce pressure within the pelvis (low pressure in pelvis and thus chamber), new fluid waste enters the chamber, thereby returning to the first stage of the cycle.

According to one embodiment of the present invention, the catheter leads from the chamber to the urinary bladder or to another location leading to discharge. The urinary bladder does not contract as the ureter does to create low pressure within the chamber. Therefore a pump is connected between the chamber and the catheter/tube to create low pressure within the chamber and thereby draw the fluid wastes through the catheter/tube for subsequent discharge. The pump is placed outside the chamber (preferably adjacent thereto) in fluid connection between the end of the catheter/tube and the interior of the chamber. Optionally, in cases where the end of the catheter ends inside the interior of the chamber, the pump may be placed within the interior of the chamber and is in fluid connection between the end of the catheter/tube and the interior space of the chamber.

According to one embodiment of the present invention, the pump is connected to the chamber on one side and to a catheter on the other side, thus enabling drainage of fluids from the chamber.

The pump capacity of fluid suction and delivery is preferably in the range of 100 CC to 5000 CC per day. The energy powering the pump can be through a battery within it, potentially rechargeable (e.g. by induction). According to one embodiment the pump is a per pump. The pump length is usually between 10 mm and 35 mm, and preferably 14 mm the pump width is usually between 10 mm and 20 mm, and preferably 14 mm. The pump height is usually between 3 mm and 4.2 mm, and preferably 3.5 mm. Example models of appropriate pumps used are piezo actuators (e.g. models mp5, mp6) of "Bartels Mikrotechnik GmbH" company.

According to an embodiment of the present invention, the fluid-penetrable chamber 5 (shown in FIG. 1) comprises a coil 10 with spring-like properties such that the coil elastically contracts and expands (other embodiments may comprise non-elastic coils) wherein the frame is actually the coil 10. In FIG. 1, the coil 10 is illustrated so that the direction of contraction and expansion is horizontal, but the coil (and its contraction and expansion) may be oriented in any direction deemed suitable by medical personnel skilled in the art. According to a preferred embodiment, the fluid-penetrable chamber 5 is implanted within the patient's abdominal cavity.

The coil 10 preferably comprises biocompatible material. The spring constant (or strength of the coil spring), the length, and the diameter of the coil may vary. Specifically, it may be constructed in accordance with factors such as the patient's space available within the abdominal cavity, the forces influencing compression of the coil (such as ureter compressions or an artificial pump, as discussed herein), and the circumferential area desired for waste passage.

The coil 10 is covered with a fluid-permeable mesh 12, thereby forming chamber 5, into which abdominal fluid (but not solids) can enter. The mesh 12 prevents bodily tissue from growing on the coil 10 and/or entering the coil 10 interior. The mesh 12 functions as a filter and enables passage of the accumulated fluids therethrough into the interior of the coil 10, while preventing the entry of anything else, such as tissue.

According to one embodiment, the mesh 12 comprises pig collagen, thereby preventing fibrosis. An example of such mesh is produced by Covidien under the name Permacol™.

The diameter of the coil 10, is usually between 2 mm and 20 mm. The length of the coil may vary, usually between 20 cm and 200 cm. The coil may be placed in the body in a folded manner, curved manner, wrapped around portions of it, etc.

Figure 3:
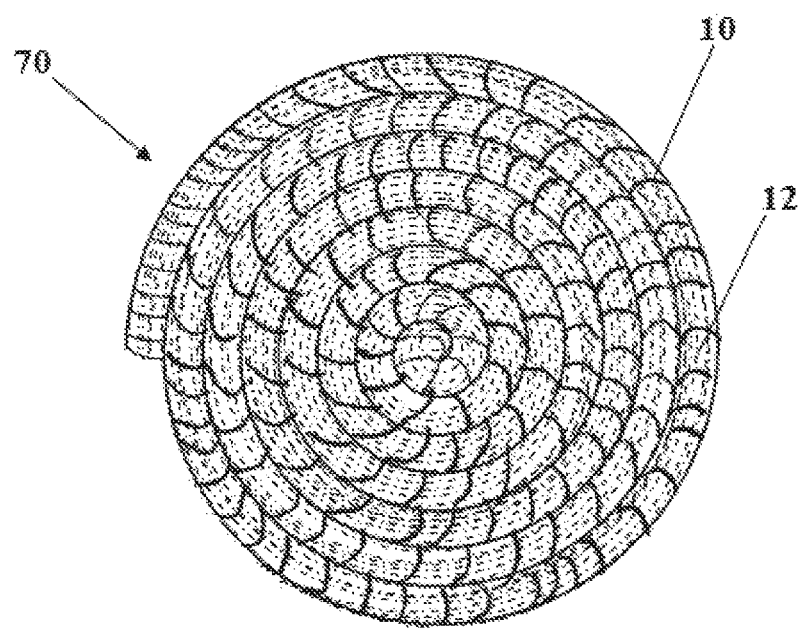
FIG. 3 illustrates an embodiment of the present invention wherein the chamber coil is curved in the form of a spiral.

According to a preferred embodiment (shown in FIG. 3), the coil 10 is curved in the form of a spiral 70 (curved which emanates from a central point, getting progressively farther away as it revolves around the point). The mesh 12 large surface area (reflected by the large spiral 70 formation) enables fluid suction therethrough into the chamber from the cavity it is placed within, and from the cavity surrounding tissue that it comes into contact with. The spiral 70 is in contact with the cavity walls. The mesh material enables suction of the fluids directly from the tissue without requiring the tissue to first eject the fluid into the cavity. This is a major advantage in cases where treatment is required to dispose of redundant bodily fluids from tissues surrounding body cavities as well as from within the cavities themselves.

The chamber 5 formed by the coil 10 is perforated by a catheter 15 which can transfer fluid therefrom into the urinary system at the location of the kidney pelvis 51 (shown in FIG. 1). According to a preferable embodiment, a pigtail catheter 15 is connected at one end to the interior of the coil 10 and is in fluid communication with the interior of the coil 10. The other end of catheter 15 is implanted within the patient's renal pelvis 51.

According to another embodiment, a straight catheter (not shown) is used instead of the pigtail catheter 15. An inflatable balloon is attached to the straight catheter near the end in the renal pelvis, for fixation and for preventing the straight catheter from slipping away from its intended position within the renal pelvis.

In use, the coil 10 may be compressed to decrease its length and then implanted into the patient's abdominal cavity. According to one embodiment, when no external forces are acting on the coil 10, it returns to its resting conformation by means of expanding. This expansion increases the space in the coil's interior. As the coil expands, the pressure within its internal space becomes reduced such that the fluid pressure within the coil 10 becomes less than that of the fluid pressure outside the coil 10, and this pressure gradient causes fluid wastes, etc., in the abdominal cavity to be drawn into the low-pressure coil cavity (through the pores in the surrounding mesh). As the coil continues to expand, more fluid wastes enter the coil 10 interior.

With reference to FIG. 1, continuous contractions of the ureter 52 lower the fluid pressure within the kidney pelvis 51. Because the kidney pelvis 51 interior is in fluid communication with the coil 10 interior by virtue of the pigtail catheter 15, the continuous ureter 52 contractions correspondingly reduce the pressure within the coil 10, thereby causing the fluid content in the interior of the coil 10 to flow through the pigtail catheter 15, into the interior of the kidney 50, and thence though the ureter 52, bladder and urethra and is thus discharged from the body. The pressure "suction" from the pelvis (or from the pump) causes coil 10 to contract.

When the ureter 52 stops contracting, the pressure inside the kidney pelvis 51 starts to accumulate and returns to its (higher) baseline pressure level. The pressure within the interior of chamber 5 (in fluid communication with pelvis 51) correspondingly increases, hence coil 10 expands. During the times within the ureter cycle following the ureter 52 acting to reduce pressure within renal pelvis 51 (and thus within the coil 10), the pressure starts to accumulate and the coil 10 expands. New fluid waste enters therein, thereby returning to the first stage of the cycle.

A compressible coil is used in this embodiment, because the compressibility reduces the strain on the ureter 51. As described above, the coil 10 is compressed to decrease its length and then implanted into the patient's abdominal cavity. However, even if the coil 10 were implanted in the abdominal cavity in its extended state, the ureter 52 would cause it to contract due to lowering the interior pressure of the pelvis 51, and then the fluid would flow from coil 10 to the kidney 50 interior and the coil 10 would begin to accumulate fluid wastes again.

Even though the pressure differences caused by the ureter 51 function affects the discharge flow, a pump 40, may optionally be connected to both catheter 15 and coil 10 for assisting in reducing the pressure within the interior of coil 10, thus assisting in delivering the fluid out of coil 10 and to the pelvis 51.

Figure 2:
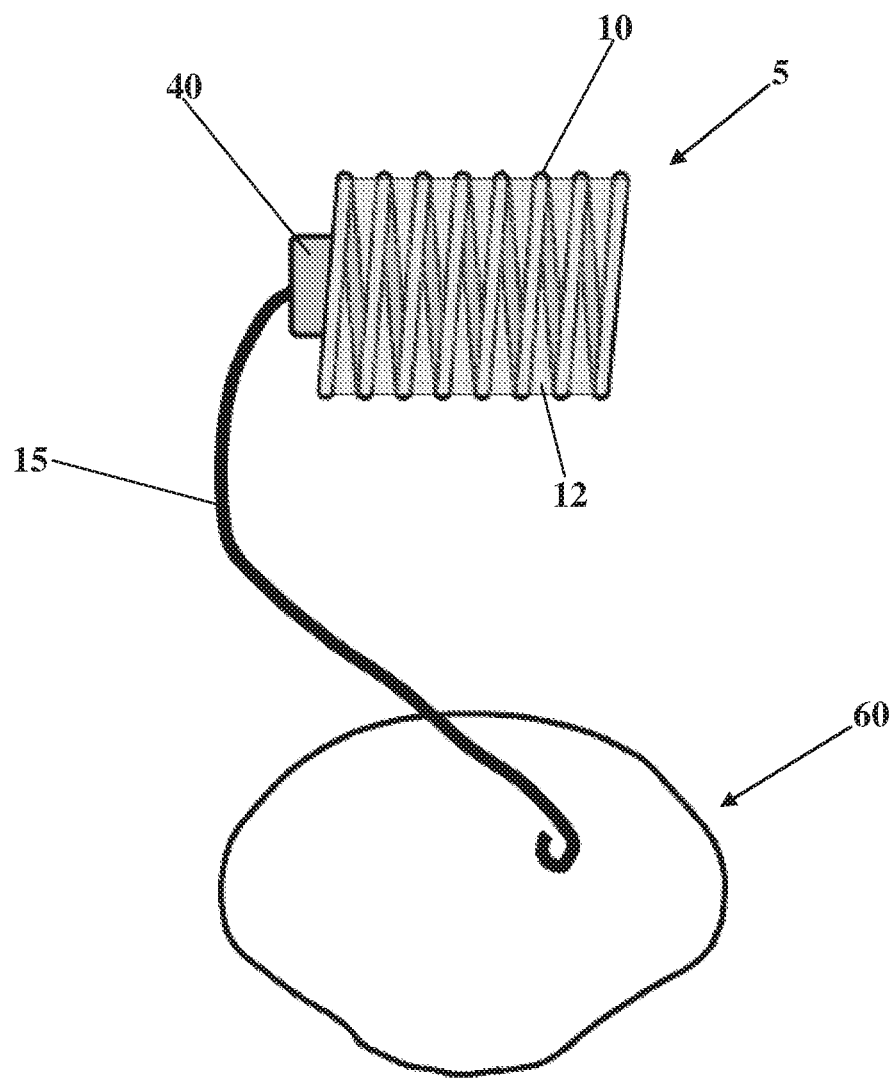
FIG. 2 illustrates an embodiment of the present invention wherein one end of the catheter is inserted into the bladder.

According to another embodiment, the chamber 5 formed by the coil 10 is perforated by the pigtail catheter 15 which can transfer fluid therefrom into the urinary system at the location of the urinary bladder 60, as illustrated in FIG. 2. One end of catheter 15 is connected to the chamber 5 interior (or side wall) and the other end other end of catheter 15 is implanted within the interior of bladder 60. The urinary bladder 60 does not contract as the ureter 52 does to create low pressure within the coil 10. Therefore a pump 40, is connected between the coil chamber 5 and the catheter (at the end of the catheter that is adjacent or within the coil 10) to create low pressure within the coil and thereby draw the fluid wastes into the bladder for subsequent discharge through the urethra.

According to another embodiment (not shown), a catheter is connected at one end to the to the chamber 5 interior (or side wall) while its other end leads out of the patient's body through a stoma, allowing direct disposal of the fluid wastes accumulated in the chamber out of the body. According to one embodiment a pump is connected to the catheter and chamber as explained hereinabove creating the low pressure within the coil (as in the previously described embodiments) causing the waste fluids to be drawn out of the chamber and out of the body. A bag may be strapped to the patient for receiving the waste fluids to enable the patient's easy mobility.

The present invention further relates to a method for draining excessive fluid from a body cavity or space, said method comprising the steps of:

a) implanting a device (as explained hereinabove) within said body cavity or space;
wherein said device (preferably) comprises an implantable fluid-penetrable chamber comprising a frame covered by a fluid permeable mesh configured to enable fluids to penetrate therethrough;
a catheter/tube connected at a first end to one of said chamber sides/wall or penetrates therethrough; and optionally further comprising a pump placed inside or outside of said chamber;

b) positioning the second end of said catheter/tube within the cavity of a urinary system organ;
such that changes in pressure within said catheter/tube and/or changes in pressure exerted within said chamber by said optional pump result in the ingress of fluid from the body cavity or space into said chamber and/or the passage of said fluid from said chamber through said catheter/tube into said urinary system organ cavity.

Preferably, the cavity of a urinary system organ is the renal pelvis.

Preferably, the cavity of a urinary system organ is the urinary bladder.

Preferably, the body cavity or space is the abdominal cavity.

Preferably, the changes in pressure within the catheter and/or changes in pressure exerted within the chamber by the optional pump result in cyclical changes in the internal volume of the fluid-penetrable chamber, thereby correspondingly assisting the ingress of fluid from the body cavity or space into said chamber, and/or thereby correspondingly assist in the passage of the fluid from said chamber through said catheter into the urinary system organ cavity.

According to a preferred embodiment of the present invention, negative pressure caused by the pump or by the pelvis (e.g. after the ureter contraction) causes contraction in internal volume of the chamber (in case of the coil-contraction of the coil) assisting the passage of the fluid from the chamber through the catheter into the urinary system organ cavity. The negative pressure also assists the ingress of fluid from the body cavity or space into the chamber.

The present invention further relates to a method for draining excessive fluid from a body cavity or space, said method comprising the steps of:

a) implanting a device (as explained hereinabove) within said body cavity or space;

wherein said device (preferably) comprises an implantable fluid penetrable chamber comprising a frame covered by a fluid permeable mesh configured to enable fluids to penetrate therethrough;

a catheter connected at a first end to one of said chamber sides/walls or penetrates therethrough; and optionally further comprising a pump placed inside or outside of said chamber;

b) positioning the second end of said catheter within a stoma in the body wall; such that changes in pressure within said catheter and/or changes in pressure exerted within said chamber by said optional pump result in the ingress of fluid from the body cavity or space into said chamber and/or the passage of said fluid from said chamber through the said body wall stoma connected to the second end of the catheter.

Preferably, the body cavity or space is the abdominal cavity.

Preferably, the changes in pressure within the catheter and/or changes in pressure exerted within the chamber by the optional pump result in cyclical changes in the internal volume of the fluid-penetrable chamber, thereby correspondingly assisting the ingress of fluid from the body cavity or space into said chamber, and/or thereby correspondingly assist in the passage of the fluid from said chamber through said catheter into the urinary system organ cavity.

EXAMPLE

The following example demonstrates the theoretical concept of die device performance in small animals.

An experiment was performed with rats using the present invention. FIG. 4A is an image of the device used in the experiment comprising a membrane mesh and a supporting spiral coil. FIG. 4B is an image of the rat with the device two weeks past implantation, a vein-flow was inserted and extracellular fluids were removed.

The efficiency of the present invention device was evaluated in four (4) rats, two weeks after implantation.

Table 1 summarizes the experimental results for 3 hr of fluids removal, in which 16±6 mL/day/Kg were retained. Based on these preliminary results, we assume that for an average adult weighting 70 Kg the present invention device could drain 1.1 L/day. It should be noted, that the fluids composition (i.e., potassium, phosphor, urea, creatinine, albumin) is analogous to rat 4 blood tests.

TABLE 1

Summary of device's efficiency in rats.

|  | Rat 1 | Rat 2 | Rat 3 | Rat 4 | Average | Blood test Rat 4 |
|---|---|---|---|---|---|---|
| Weight [kg] | 0.420 | 0.320 | 0.350 | 0.376 | 0.367 ± 0.042 |  |
| CC/3 Hrs | 0.400 | 0.600 | 1.000 | 0.800 | 0.700 ± 0.258 |  |
| L/Day/Kg | 0.008 | 0.015 | 0.023 | 0.017 | 0.016 ± 0.006 |  |
| L/Day/70 Kg | 0.533 | 1.050 | 1.600 | 1.191 | 1.094 ± 0.440 |  |
| Diameter [cm] | 0.4 | 0.4 | 0.4 | 0.4 |  |  |
| Length [cm] | 6 | 5 | 5 | 3 |  |  |
| Potassium [mmol/L] | 12.7 | 5.3 | 5.8 | 7.000 | 7.700 ± 3.409 | 6.5 |
| Phosphor [mg/dL] | 9.7 | 6.8 | 8.7 | 9.800 | 8.750 ± 1.392 | 9 |
| Urea [mg/dL] | 37.6 | 37.4 | 34.9 | 44.900 | 38.700 ± 4.312 | 50.9 |
| Creatinine [mg/dL] | 0.3 | 0.36 | 0.35 | 0.410 | 0.355 ± 0.045 | 0.46 |
| Albumin [g/dL] | 2.6 | 3.1 | 3.5 | 3.1 | 3.075 ± 0.369 | 3.9 |

| 70 kg | Urea blood | Output 2 L/day | Extracellular fluids | Per dialysis [gr] | Weekly [gr] |
|---|---|---|---|---|---|
| Urea potential | 100 | 2 |  |  | 14 |
| Urea hemodialysis | 100 |  | 35 | 22.75 | 68.25 |

Having thus described exemplary embodiments of the invention, it will be apparent that various alterations, modifications, and improvements will readily occur to those skilled in the art. For example, although embodiments are described above in which a device for draining substances from the body is implanted within a patient's abdominal cavity, in other embodiments a device may be implanted subdermally, in the retroperitoneum, or in the pleural cavity, as non-limiting examples. The present invention may be implanted in other body cavities or spaces. Another example variation of embodiments described above involves constructing the fluid penetrable chamber without the separate mesh but instead in such a way that tissue cannot penetrate the chamber exterior but fluids can. Further example variations of embodiments described above involve treating conditions such as cancer, cardiac insufficiency (e.g. DHF in advanced stages), or ascites due to liver cirrhosis, that is, conditions in which their treatments involve fluid drainage.

While some of the embodiments of the invention have been described by way of illustration, it will be apparent that the invention can be carried into practice with many modifications, variations and adaptations, and with the use of numerous equivalents or alternative solutions that are within the scope of a person skilled in the art, without departing from the spirit of the invention, or the scope of the claims.

The invention claimed is:

1. A system comprising:
an implantable fluid penetrable chamber comprising a frame having flat permeable sides, wherein said frame is covered by a fluid permeable membrane mesh configured to enable fluids of a tissue contacting said fluid permeable membrane mesh to penetrate directly from said tissue into said implantable fluid penetrable chamber through said flat permeable sides; a catheter connected at a first end to one side of said chamber or penetrates therethrough;
and further comprising a pump placed inside or outside of said chamber.

2. The system according to claim 1, wherein the volume of the chamber is capable of expanding and contracting in response to changes in pressure within the catheter and/or as a result of the activity of the pump.

3. The system according to claim 1, wherein the pump is connected between the chamber and the catheter.

4. The system according to claim 1, wherein the pump is a peristaltic pump.

5. The system according to claim 2, wherein the frame is a coil with spring-like properties such that said coil is configured to elastically contract and expand.

6. The system according to claim 5, wherein the coil comprises biocompatible material.

7. The system according to claim 5, wherein the coil is curved in the form of a spiral in which said coil emanates from a central point, getting progressively farther away as it revolves around the point, wherein said spiral curved coil forms a planar spiral frame emanating from a central point and is covered by said fluid permeable mesh.

8. The system according to claim 1, wherein the membrane mesh is made of material selected from the group consisting of Teflon, Polypropylene, Polyester, ePTFE, titanium, omega 3, monocryl, PVDF, hyaluronate and Gortex, acellular collagen, pig collagen, a matrix derived from human dermis and porcine small intestine submucosa.

9. The system according to claim 1, wherein the catheter is a pigtail catheter.

10. The system according to claim 1, wherein said catheter is a straight catheter comprising an inflatable balloon attached at or near a second end of said catheter.

11. A method for draining excessive fluid from a body cavity or space, said method comprising the steps of:
a) implanting a device within said body cavity or space; wherein said device comprises an implantable fluid penetrable chamber comprising a frame having flat permeable sides covered by a fluid permeable membrane mesh configured to encourage fluids of a tissue contacting said fluid permeable membrane mesh to penetrate directly from said tissue into said chamber through said flat permeable sides;
a catheter connected at a first end to one side of said chamber or penetrates therethrough;
and further comprising a pump placed inside or outside of said chamber;
b) contacting at least part of a tissue by said fluid permeable membrane mesh covering said chamber;
c) positioning the second end of said catheter within the cavity of a urinary system organ;
such that changes in pressure within said catheter and/or changes in pressure exerted within said chamber by said pump result in the ingress of fluid from tissue contacting said flat permeable sides directly into said chamber.

12. The method according to claim 11, wherein the cavity of a urinary system organ is the renal pelvis.

13. The method according to claim 11, wherein the cavity of a urinary system organ is the urinary bladder.

14. The method according to claim 11, wherein the body cavity or space is the abdominal cavity.

15. The method according to claim 11, wherein the changes in pressure within the catheter and/or changes in pressure exerted within the chamber by the pump result in cyclical changes in the internal volume of the fluid penetrable chamber, to encourage the ingress of fluid from the body cavity or space into said chamber, and/or to encourage the passage of the fluid from said chamber through said catheter into the urinary system organ cavity.

16. A method for draining excessive fluid from a body cavity or space, said method comprising the steps of:
a) implanting a device within said body cavity or space; wherein said device comprises an implantable fluid penetrable flat chamber comprising a frame, said flat chamber having flat permeable sides surrounded by a fluid permeable membrane mesh configured to encourage fluids of a tissue contacting said fluid permeable membrane mesh to penetrate directly from said tissue into said flat chamber through said flat permeable sides;
a catheter connected at a first end to one side of said flat chamber or penetrates therethrough;
and further comprising a pump placed inside or outside of said chamber;
b) draining excessive fluid by contacting at least part of a tissue by said fluid permeable membrane mesh surrounding said chamber.

17. The system according to claim 1, wherein said membrane mesh is made from a material which prevents tissue growth on said flat chamber.

18. The system according to claim 1, wherein said membrane mesh is not permeable to tissue.

19. A system comprising:
an implantable fluid penetrable chamber comprising a planar spiral frame which emanates from a central point and getting progressively farther away as it revolves around the point, wherein said planar spiral frame is covered by a fluid permeable membrane mesh configured to enable fluids to penetrate therethrough;
a catheter connected at a first end to one side of said chamber or penetrates therethrough;
and further comprising a pump placed inside or outside of said chamber.

* * * * *